(12) United States Patent
Possinger et al.

(10) Patent No.: US 9,683,792 B2
(45) Date of Patent: Jun. 20, 2017

(54) FLOATING THERMAL CONTACT ENABLED PCR

(71) Applicant: GnuBio, Inc., Cambridge, MA (US)

(72) Inventors: Christopher Possinger, Cambridge, MA (US); Sepehr Kiani, Cambridge, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 7 days.

(21) Appl. No.: 14/755,941

(22) Filed: Jun. 30, 2015

(65) Prior Publication Data

US 2015/0375229 A1 Dec. 31, 2015

Related U.S. Application Data

(60) Provisional application No. 62/018,893, filed on Jun. 30, 2014.

(51) Int. Cl.
| | |
|---|---|
| *C12M 1/00* | (2006.01) |
| *C12Q 1/68* | (2006.01) |
| *C12P 19/34* | (2006.01) |
| *C07H 21/02* | (2006.01) |
| *G01N 25/00* | (2006.01) |
| *F28F 13/14* | (2006.01) |
| *B01L 7/00* | (2006.01) |
| *F25B 21/04* | (2006.01) |
| *B01L 3/00* | (2006.01) |

(52) U.S. Cl.
CPC ............. *F28F 13/14* (2013.01); *B01L 7/525* (2013.01); *C12P 19/34* (2013.01); *B01L 3/502784* (2013.01); *B01L 2300/0816* (2013.01); *B01L 2300/0883* (2013.01); *B01L 2300/1805* (2013.01); *B01L 2300/1822* (2013.01); *B01L 2300/1883* (2013.01); *F25B 21/04* (2013.01); *F28F 2270/00* (2013.01); *F28F 2275/20* (2013.01)

(58) Field of Classification Search
CPC .... C12P 19/34; B01L 4/502784; B01L 7/525; F28F 13/14
USPC ......... 435/6.1, 91.2, 283.1, 303.1; 536/23.1; 422/82.12
See application file for complete search history.

(56) References Cited

U.S. PATENT DOCUMENTS

| | | | |
|---|---|---|---|
| 5,475,610 A * | 12/1995 | Atwood ............. | G05D 23/1935 422/943 |
| 6,786,691 B2 | 9/2004 | Alden, III | |
| 7,741,123 B2 | 6/2010 | Pease et al. | |
| 8,088,616 B2 * | 1/2012 | Handique ......... | B01L 3/502715 435/287.1 |
| 8,151,589 B2 | 4/2012 | Lepschi et al. | |
| 8,528,589 B2 | 9/2013 | Miller et al. | |
| 8,535,889 B2 | 9/2013 | Larson et al. | |
| 2010/0104485 A1 | 4/2010 | Yuan | |
| 2011/0057117 A1 | 3/2011 | Fawcett et al. | |
| 2011/0151578 A1 | 6/2011 | Abate et al. | |
| 2011/0218123 A1 | 9/2011 | Weitz et al. | |
| 2011/0250597 A1 | 10/2011 | Larson et al. | |
| 2011/0267457 A1 | 11/2011 | Weitz et al. | |
| 2012/0015822 A1 | 1/2012 | Weitz et al. | |
| 2012/0132288 A1 | 5/2012 | Weitz et al. | |
| 2012/0219947 A1 | 8/2012 | Yurkovetsky et al. | |
| 2012/0220494 A1 | 8/2012 | Samuels et al. | |
| 2012/0222748 A1 | 9/2012 | Weitz et al. | |
| 2012/0309002 A1 | 12/2012 | Link | |
| 2013/0217103 A1 | 8/2013 | Bauer | |
| 2013/0344485 A1 | 12/2013 | Raz et al. | |
| 2014/0198313 A1 | 7/2014 | Tracy et al. | |
| 2014/0354795 A1 | 12/2014 | Tracy et al. | |
| 2015/0024945 A1 | 1/2015 | Healy | |
| 2015/0045258 A1 | 2/2015 | Raz et al. | |
| 2015/0065396 A1 | 3/2015 | Kiani et al. | |
| 2015/0093815 A1 | 4/2015 | Kiani et al. | |
| 2015/0094232 A1 | 4/2015 | Abate et al. | |
| 2015/0209785 A1 | 7/2015 | Esmail et al. | |

FOREIGN PATENT DOCUMENTS

| | | |
|---|---|---|
| EP | 2364774 A2 | 9/2011 |
| EP | 2662135 A2 | 11/2013 |
| WO | 2007/081385 A2 | 7/2007 |
| WO | 2007/081387 A1 | 7/2007 |
| WO | 2012/078710 A1 | 6/2012 |
| WO | 2012/135201 A1 | 10/2012 |
| WO | 2012/135259 A1 | 10/2012 |
| WO | 2012/135327 A1 | 10/2012 |
| WO | 2013/095737 A2 | 6/2013 |
| WO | 2013/122826 A1 | 8/2013 |
| WO | 2013/165748 A1 | 11/2013 |
| WO | 2014/043388 A1 | 3/2014 |
| WO | 2014/093976 A1 | 6/2014 |
| WO | 2014/117088 A1 | 7/2014 |
| WO | 2014/176599 A1 | 10/2014 |

OTHER PUBLICATIONS

Unpublished U.S. Appl. No. 14/652,094, filed Jun. 12, 2015, to GnuBio, Inc., titled Method for Maintaining Heterogeneous Concentrations of Molecules in Emulsion Droplets.
Unpublished U.S. Appl. No. 14/762,617, filed Jul. 22, 2015, to Gnubio, Inc., titled System and Method for Performing Droplet Inflation.
International Search Report and Written Opinion mailed Sep. 23, 2015, from International Application No. PCT/US2015/038525 (12 pages).

* cited by examiner

*Primary Examiner* — Narayan Bhat
(74) *Attorney, Agent, or Firm* — Kilpatrick Townsend and Stockton LLP

(57) ABSTRACT

The present invention generally pertains to a system which utilizes floating thermal contact to enable PCR, in a thermal management device. Comprised of multiple thermal zones attached to a framework, each zone an individually actuated, isolated sub-assembly. The actuation of each zone ensures physical contact with an uneven, yet flat microfluidic chip to achieve effective, conductive heat transfer. The isolation of each zone serves to insulate the thermal zones from each other and minimize undesired heat transfer between adjacent zones, so that each zone is at a proper, uniform temperature.

20 Claims, 7 Drawing Sheets

FLOATING THERMAL CONTACT ENABLED PCR

CROSS-REFERENCE TO RELATED APPLICATIONS

This application claims priority to and the benefit of U.S. Provisional Application No. 62/018,893, entitled "FLOATING THERMAL CONTACT ENABLED PCR", filed on Jun. 30, 2014, the disclosure of which is hereby incorporated by reference.

FIELD OF THE INVENTION

The present invention is in the technical field of molecular biology and instrumentation.

BACKGROUND OF THE INVENTION

One can cycle the temperature of a Polymerase Chain Reaction (PCR) device for DNA replication in a reacting volume by physically moving the volume through separate heat zones of a microfluidic device by using a channel of suitable length and geometry. Typical PCR systems have fluids in a relatively large chamber and cycle the temperature around the chamber. Other systems use flexible tubing to cycle fluids past heated zones. A problem with conducting PCR in rigid, planar microfluidic devices is that it can be difficult to make a good thermal connection, and thus the results can be inconsistent and unreliable. In order to reduce costs and manufacturing complexity, it is desirable for the thermal management system be an external device that can be attached to the microfluidic assembly. The number of thermal zones on the microfluidic device, the temperature ranges of the thermally active zones, and the zone's proximity to each other all restrict the design choices that can be made concerning a thermal management device. The following invention uses floating thermal contacts to enable PCR reactions. Described, is a device for managing the heating and cooling of multiple areas on an external part or assembly, through the use of isolated, movable, and conductive zones, thereby enabling very efficient PCR reactions. Citation or identification of any document in this application is not an admission that such document is available as prior art to the present invention.

BRIEF SUMMARY OF THE INVENTION

The present invention generally pertains to a system which utilizes floating thermal contacts in a thermal management device to enable PCR in a coupled microfluidic device. The thermal management device includes multiple thermal zones attached to a framework, where each zone is an individually actuated, isolated sub-assembly. The actuation of each zone ensures physical contact with an uneven, yet flat microfluidic chip to achieve effective, conductive heat transfer. The isolation of each zone serves to insulate the thermal zones from each other and minimize undesired heat transfer between adjacent zones, so that each zone is at a proper, uniform temperature.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

"Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

In some embodiments, the present disclosure is directed to a thermal management device for enabling PCR reactions in a microfluidic channel, where the device includes a framework; one or more thermal zone sub-assemblies coupled to the framework, where each thermal zone sub-assembly can have a thermal control element, and where each thermal zone sub-assembly can be coupled to the framework by one or more thermal actuation mechanisms; and one or more thermal spreaders are configured to contact the thermal control elements of the one or more thermal zone sub-assemblies. A microfluidic device in which PCR can be performed can be mounted on or mechanically coupled to the thermal management device.

In some implementations, the thermal actuation mechanisms further comprise insulative bearings, fasteners, and a spring, where the spring is configured to apply a force to drive the thermal control element toward one of the one or more thermal spreaders. In some aspects, the insulative bearings are polymer-based bearings. In other aspects, each fastener is a shoulder screw, and each thermal actuation mechanisms includes at least one polymer-based bearing, where the bearing can travel up and down on the shaft of the shoulder screw that is attached to the framework, which can be pushed (in some configurations, upward) by the spring. In further aspects, each thermal control element can be configured to have an operational temperature of from about 22° C. to about 95° C. In some aspects, each of the thermal actuation mechanisms further includes a first insulative fiber washer around the shoulder screw that holds the spring in place. In such aspects, the bearing can include a flange that spreads at one end of the bearing in contact with the framework. In other aspects, each thermal zone sub-assembly has a minimal spacing of 1 mm between itself and any other thermal zone sub-assembly or the framework.

In some embodiments, at least one thermal zone assembly has a resistive heating element used to maintain a thermal zone at a temperature above room temperature. In further embodiments, at least one thermal zone assembly has a thermoelectric element used to maintain a thermal zone at a temperature at or below room temperature. In such aspects, at least one thermal zone assembly maintains a thermal zone at a temperature above room temperature, and at least another thermal zone assembly maintains a thermal zone at a temperature at or below room temperature. In some implementations, a first thermal zone and a fifth thermal zone are maintained at a temperature at or below room temperature, a second thermal zone, fourth thermal zone, and a sixth thermal zone are maintained at a temperature above room temperature, and a third thermal zone is maintained at a temperature above the temperature of at least the second thermal zone. In some aspects, at least one of the thermal zone sub-assemblies is coupled to a heat sink. In such aspects, the heat sink can be a finned heat sink, at least one of the thermal zone sub-assemblies can be remotely connected to a heat sink via a heat pipe, and alternatively or additionally at least another of the thermal zone sub-assemblies can directly mounted on a heat sink.

In further embodiments, a flexible heater circuit is configured and arranged to be the thermal control element for two or more thermal zone sub-assemblies of the thermal management device. In some aspects, a first region of the flexible heater circuit can be moved by one of the thermal actuation mechanisms to be in contact with one of the thermal spreaders. In other aspects, the first region of the flexible heater circuit is in contact with one of the thermal spreaders and at least a second region of the flexible heater circuit is in contact with one of the thermal spreaders. In further aspects, the first region of the flexible heater circuit and the second region of the flexible heater circuit can flex relative to each other by a distance of about 0.75 mm to about 1.0 mm.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
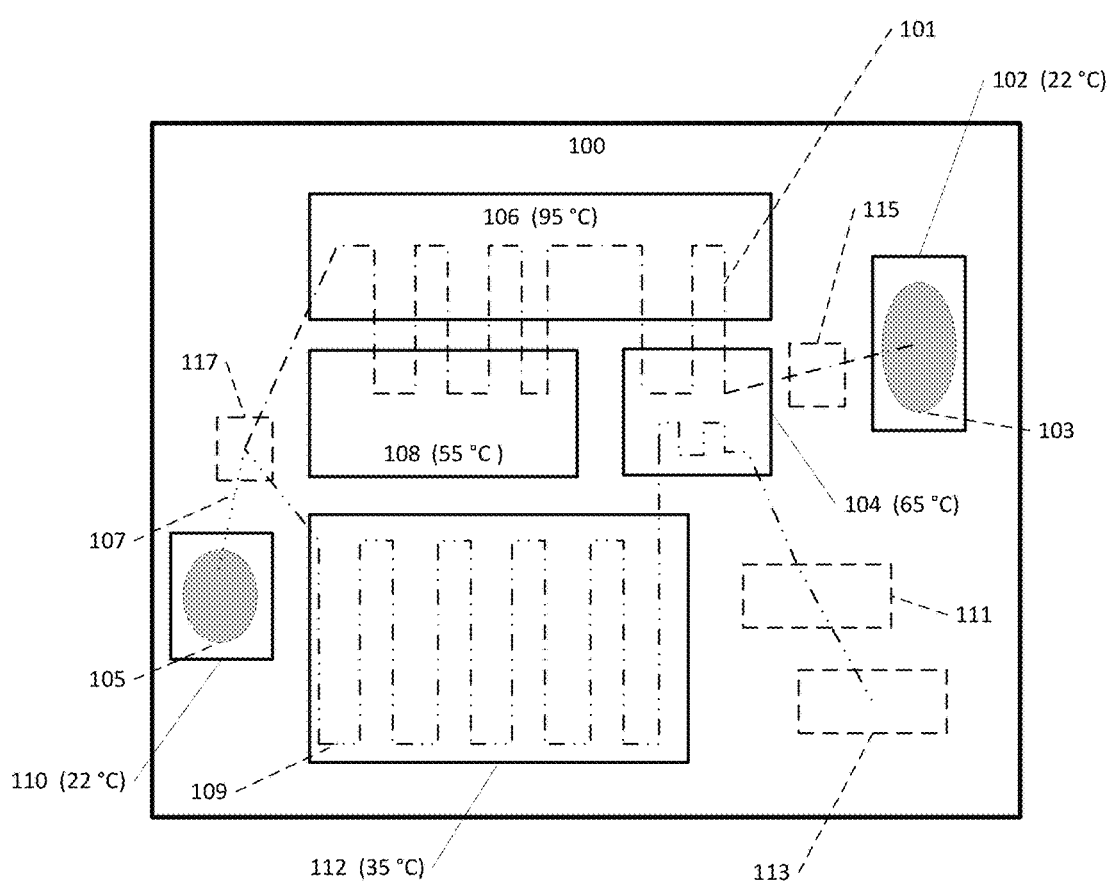
FIG. 1 is a schematic layout of the thermal zones used for PCR as arranged in a thermal management device, labeled with an exemplary temperature indicated for each zone, according to aspects of the present disclosure.

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

To replicate DNA using the Polymerase Chain Reaction (PCR) method, a reacting volume is cycled through a series of different temperatures to start or stop different chemical reactions. Traditionally, this is achieved by utilizing a thermoelectric module to both heat and cool the reacting volume. This thermal cycling can also be achieved by moving the reacting volume through multiple zones held at different temperatures. One common solution is to have a coil of flexible tubing wrapped around thermal zones, in which the flexible tubing conforms to the thermal zones. To move very small reaction volumes, one can utilize a microfluidic device with channels of suitable length and geometry, typically in an integrated, planar microfluidic circuit. However, these devices are typically rigid, which makes it difficult to achieve good thermal contact with a thermal management system's thermal zones. The present disclosure provides for structures and methods to ensure each thermal zone of a thermal management device effectively makes contact with the microfluidic device at operative temperatures.

A microfluidic device (alternatively referred to as a cartridge) as considered herein can be a body with a series of reservoirs for storing and receiving different chemical reagents, which are supplied to a microfluidic "chip" that is bonded to the body. In some aspects, the reagents can be provided to a sample fluid as a plurality of droplets. The microfluidic chip can be a relatively flat part of the device which contains a multitude of micrometer-level channels and other plumbing features which facilitate different chemical reactions. The result of these reactions, in exemplary embodiments of the present disclosure, can be analyzed to determine the DNA sequence of a specific gene or genes. In order to supply or remove heat for these chemical reactions, This microfluidic device can be inserted into a thermal management system, where the individual thermal zone sub-assemblies of the thermal management device can adjust and move into an operative position, directly contacting regions of the microfluidic device. Each individual thermal zone sub-assembly can have one or more thermal zone actuation mechanisms to adjust and move the thermal elements, such as heat spreading elements, into contact with the microfluidic device at specific locations.

The geometry of a microfluidic device, including the size and shape of its thermally active zones, creates a number of challenges in designing a thermal management device. It is difficult to produce a microfluidic part or multi-zone thermal device that has a high enough degree of flatness to ensure proper contact and conduction between the microfluidic device and the different zones. Variation in the flatness of a microfluidic part can simply be a result of unavoidable mechanical variation that is still within manufacturing tolerances. The thermal zones themselves are very close together, and in some instances it is desirable for them to be as close to one another as possible in order to achieve a reaction in sample passing between the thermal zones. For example, the temperatures of neighboring zones can have a sharp temperature gradient of 40° C. per millimeter or higher. Generally, during operation, the thermal zones can be at temperatures of 35° C. or higher, and can be referred to as heating thermal control zones. In some cases, some of the temperature zones are required to heat and elevate to a temperature of 35° C. or higher, but other thermal control zones may be cooled to lower than 25° C. (room temperature). Cooling thermal control zones, for example, can operate to preserve perishable reagents held within a microfluidic device that would be damaged by long exposure to relatively higher temperatures.

Conduction, which can only occur via a direct, physical contact, is the most efficient form of heat transfer between solids and liquids. For conduction to exist in this case there must be contact between the microfluidic device and the thermal management device. As noted previously, it is difficult to ensure contact over large surface areas, especially in multi-element assemblies interacting with a plastic or glass-based microfluidic device. Some approaches to distributing heat over large surface areas have used a thermally conductive fluid or a thermal grease between a microfluidic device and a thermal source, but such implementations are complex and require significant maintenance. To adequately and accurately distribute heat over a sufficient surface area, the thermal zones of the present disclosure are all independently actuated, so that they can conform to any local or global non-flatness in the microfluidic device.

In order to individually actuate each zone, it is useful to make each zone a separate sub-assembly, which allows for each zone to be thermally isolated from the other zones. In one embodiment of the invention, each zone has a minimal spacing of on millimeter (1 mm) between itself and any other zone or the framework of the device that the zones are attached to. The invention provides multiple bearing and shaft elements for each zone, which can be referred to as thermal zone actuation mechanisms. To further insulate each thermal zone from the framework, the invention can use thermal insulative bearings, for example, polymer based bearings, and non-thermally-conductive washers which have much lower rates of conduction than any metal equivalent. This configuration limits the heat transfer paths available for each zone to the following and thus improves the energy efficiency of the thermal management device.

In other words, a strong conduction of heat to specific sections of the microfluidic device is maintained via direct contact to the individual thermal sub-assemblies. Relatively weaker thermal gradients can still exits at least in part due to, for example: convection in the air gaps between each zone; conduction between each zone and the supporting framework of the thermal management device via an insulated fiber washer; and/or conduction between each zone and the supporting framework via a polymer bearing and a stainless steel shoulder screw coupling the thermal management device sub-assemblies together.

Various heating elements are used to meet the different temperature requirements for different thermal zones of the device. Some of the heating elements are mounted directly or remotely to heat sinks (such as finned heat sinks) to increase thermal mass and facilitate convective heat transfer from the zones to the environment. Heating elements can be resistive heaters, Peltier heaters, or the like.

When a microfluidic device is inserted, connected, and/or coupled to the thermal management device, a spring load in each thermal zone actuation mechanism pushes the heating and/or cooling elements of each thermal zone sub-assembly into direct contact with the related thermal zones on the microfluidic device. This ensures good contact and therefore good conduction of heat into the microfluidic chip.

FIG. 1 is a schematic layout of the thermal zones used for PCR as arranged in an exemplary thermal management device 100, labeled with an exemplary temperature indicated for each thermal zone. Generally, it is assumed that the system is operating in an environment that is at a standard 25° C. room temperature, or slightly above. Some of the thermal control zones (e.g. regions set to about 22° C. or about 35° C.) can be heated and/or cooled by a thermoelectric element. Some of the thermal control zones that are raised to relatively higher temperatures (e.g. regions set to about 95° C.) can be heated by resistive heating elements. In some implementations, each thermal zone of the thermal management device is related to an individual thermal control sub-assembly. In some embodiments, each thermal control zone of the thermal management device is individually and separately controlled.

The thermal management device 100 has a plurality of thermal control zones that can be used for heating and/or cooling. A device, containing a microfluidic chip (elements of which are shown overlaid on the thermal management device 100), can be inserted into a PCR device above and proximate to the thermal management device 100, where the microfluidic chip can have one or more channels that align to pass over specific thermal control zones of the thermal management device 100. Thus, samples to be amplified and/or sequenced move through regions via the one or more channels (alternatively referred to as serpentine PCR), as opposed to a single thermal block ramping up and down in temperature.

Once mounted within the PCR device, the sample on the microfluidic chip is positioned above a first thermal zone 102 (alternatively referred to as the sample cooling zone), where the sample is in a primary reservoir 103 on the microfluidic device. The first thermal zone 102 can cool or maintain the temperature of the sample in the primary reservoir 103 at a temperature of about 22° C.±4° C. Additional samples, reagents, buffers, oils, and/or other fluids or materials can also be stored on the microfluidic device. The sample fluid is directed out from the primary reservoir 103 through a first channel section 101 (alternatively referred to as an upper serpentine region) of the microfluidic chip. The additional samples, reagents, buffers, oils, and/or other fluids or materials can be added to the sample in the first channel section 101, and reactions can take place within the first channel section 101. The sample can be in the form of droplets as it passes though the microfluidic chip channels. In alternative embodiments, additional samples, reagents, buffers, oils, and/or other fluids or materials can be added to the sample within the primary reservoir 103. In further alternative embodiments, the sample can be injected into already existing droplets on the chip having relevant reagents, buffers, oil, and the like. In yet further embodiments, the sample can have PCR carried out within large drops (referred to as "slugs") which can subsequently be injected into pre-existing droplets on the microfluidic chip post-PCR.

The sample is directed out of the primary reservoir 103 and away from the first thermal zone 102 through the first channel section 101, and after various reagents are added and reactions occur (in zones of the microfluidic chip not shown), the sample enters a second thermal zone 104 (alternatively referred to as a primary extension zone) and a third thermal zone 106 (alternatively referred to as a denature zone). In some implementations, the sample is routed through the upper serpentine to pass over the denature zone for a period of time before passing over the primary extension zone. As the first channel section 101 alternatingly passes over the second thermal zone 104 and third thermal zone 106, the sample cycles through the thermal gradient between the second thermal zone 104 and third thermal zone 106, which can be set to facilitate PCR. In some implementations the second thermal zone 104 can be set to a temperature of about 65° C.±2° C. In some implementations the third thermal zone 106 can be set to a temperature of about 95° C.±5° C. In some specific implementations the third thermal zone 106 can be set to a temperature of about 98° C.±2° C. The first channel section 101 can continue to direct sample toward a fourth thermal zone 108 (alternatively referred to as a secondary extension zone), and alternatingly pass over the third thermal zone 106 and the fourth thermal zone 108, such that the sample cycles through the thermal gradient between the third thermal zone 106 and the fourth thermal zone, which can be set to further facilitate PCR. In some implementations the fourth thermal zone 108 can be set to a temperature of about 55° C.±6° C. In some specific implementations the fourth thermal zone 108 can be set to a temperature of about 51° C.±2° C.

After passing through the first channel section 101, the sample can be injected with additional temperature controlled reagent(s), such as an enzyme solution, along with other, non-temperature controlled reagents, to facilitate sequencing reactions. The temperature controlled sequencing reagent(s) can be held in a secondary reservoir 105 on the microfluidic device and can be introduced, along with the other reagents, into the sample through an injection channel 107. The secondary reservoir 105 can be positioned over a fifth thermal zone (alternatively referred to as an enzyme cooling zone), which can cool or maintain the temperature of the sequencing reagents (e.g. enzyme solution) in the secondary reservoir 105 at a temperature of about 22° C.±4° C. Once injected with sequencing reagents, the sample proceeds through a second channel section 109 (alternatively referred to as a lower serpentine region) of the microfluidic chip.

The second channel section 109 of the microfluidic chip can pass over a sixth thermal zone 112 (alternatively referred to as sequencing incubation zone) that can be set to a temperature of about 34° C.±2° C. In some specific implementations the sixth thermal zone 112 can be set to a temperature of about 35° C.±1° C. While the sample passes through the second channel section 109 at a temperature at or near the temperature of the sixth thermal zone 112, the sample can undergo sequencing reactions. The second channel section 109 can progress from the sixth thermal zone 112 back to the second thermal zone 104 such that the sequencing reactions can complete at about the temperature of the second thermal zone 104. The amplified and sequenced sample can then progress through the second channel section 109 to an optical detection region 111 where the sample can be observed, measured, and/or characterized. After passing through the optical detection region 111, the sample can be routed to a waste reservoir 113. Either or both of the optical detection region 111 and the waste reservoir 113 can be located on the microfluidic chip. In some embodiments, either or both of the optical detection region 111 and the waste reservoir 113 can be located on the microfluidic device, but off the microfluidic chip. In alternative embodiments, the optical detection region 111 and the waste reservoir 113 can be located in the PCR device, off of the microfluidic device. In some implementations, the optical detection region 111 is located on the microfluidic chip and the waste reservoir 113 on the microfluidic device but off of the microfluidic chip.

Each of the various thermal control zones of the thermal control device 100 can be individual sub-assemblies having a thermal control element, a support framework, guide screw, a spring, and a thermal spreader element configured to contact a specific region of a microfluidic device when the microfluidic device is mounted within a PCR device. The individual sub-assemblies can also be coupled to heat sinks and/or insulators. In various configurations, each of the first thermal zone 102, second thermal zone 104, third thermal zone 106, fourth thermal zone 108, fifth thermal zone 110, and sixth thermal zone 112 can be directly coupled to an insulating material. In further configurations, each of the first thermal zone 102, second thermal zone 104, third thermal zone 106, fourth thermal zone 108, fifth thermal zone 110, and sixth thermal zone 112 can be directly coupled to a heat sink. In further alternative configurations, each of the first thermal zone 102, second thermal zone 104, third thermal zone 106, fourth thermal zone 108, fifth thermal zone 110, and sixth thermal zone 112 can be indirectly coupled to a heat sink via a heat conducting element such as a heat pipe. For thermal zones indirectly coupled to a heat sink as disclosed herein, the coupling can be through one heat pipe, two heat pipes, or three or more heat pipes. In some implementations of the present disclosure, the third thermal zone 106 can be coupled to an insulating material, the first thermal zone 102, second thermal zone 104, and fourth thermal zone 108 can be directly coupled to respective heat sinks, and the fifth thermal zone 110, and sixth thermal zone 112 can be indirectly coupled to respective heat sinks.

In some embodiments, the microfluidic chip can further include intermediate observations regions. In some aspects, a primary observation region 115 can be positioned along the first channel section 101 before the sample actually enters the upper serpentine portion of the channel. The primary observation region 115 can be configured to measure and observe the overall fluid as reagents for PCR are added to the sample. Similarly, in other aspects, a secondary observation region 117 can be positioned proximate to the interface of the first channel section 101, the injection channel 107, and the second channel section 109 before the sample actually enters the lower serpentine portion of the channel. The secondary observation region 117 can be configured to measure and observe the overall fluid as reagents for sequencing are added to the sample. The optical detection region 111 remains at a position post-sequencing for measuring and observing the sequenced sample.

Figure 2A:
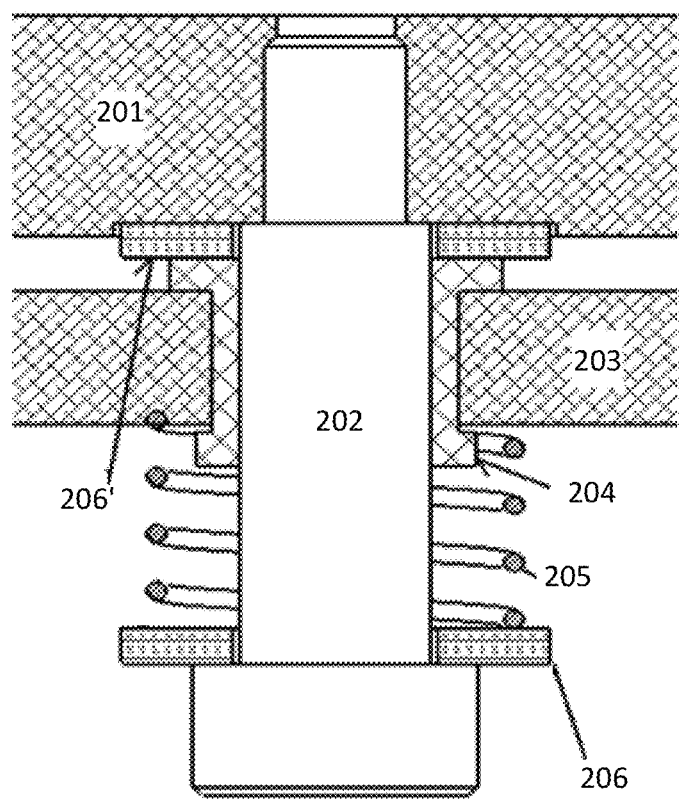
FIG. 2A is a cross-sectional schematic view of a thermal zone actuation mechanism for a thermal management device used for microfluidic chip PCR, according to aspects of the present disclosure.

FIG. 2A is a cross-sectional schematic view of a thermal zone actuation mechanism 200 for a thermal management device used for microfluidic chip PCR. In some embodiments, each thermal control zone has three to five (3-5) thermal zone actuation mechanisms 200 arranged as part of the sub-assemblies, spaced to balance an overall spring force at or near the center of each thermal zone. A framework 201 is a stationary element both providing support to a microfluidic device and a mounting structure for each thermal zone actuation mechanism 200. For each thermal zone actuation mechanism 200, a shoulder screw 202 is attached to the overall thermal framework 201 via a tapped hole. A thermal module base plate 203, as shown herein as a insulative thermal module base plate 203 can extend across at least a part of the area of a thermal zone, having holes in the thermal module base plate 203 into which the polymer bearing 204 is inserted. As shown herein, the thermal module base plate 203 can be a single part component, though in further embodiments a larger or multi-part thermal module can be positioned where the thermal module base plate 203 is implemented in FIG. 2A and FIG. 2B. The hole in the polymer bearing 204 allows to allow for a shoulder screw 202 to pass through. In some aspects, the thermal module base plate 203 can be mechanically and/or thermally coupled to a thermal source or heating element, such that the thermal module base plate 203 can control the conduction of heat to thermal spreading elements coupled to the thermal zone actuation mechanism 200. The bearings 204 allow for the thermal module base plate 203 to travel up and down along the shaft of the shoulder screws 202 in a thermal zone subassembly. In each thermal zone actuation mechanism 200, either or both of the bearing 204 and the thermal module base plate 203 are operatively coupled to and are pushed upward by a spring 205. Accordingly, because the location of a thermal module base plate 203 along the length of a shoulder screw 202 is variable, with a spring force from the one or more springs 205 in the thermal zone pushing upward on the thermal module base plate 203, and with any weight or load (such as a microfluidic chip) exerting a force downward on the thermal module base plate 203 via the framework 201, the thermal insulator 203 and bearing 204 can be said to be "floating" with respect to the framework 201 as they provide contact to various loads placed on the framework 201.

In some embodiments, a first insulative fiber washer 206 and a second insulative fiber washer 206' can be located around the shoulder screw 202. In particular, the second insulative fiber washer 206' can be positioned in between the thermal module base plate 203 and the framework 201, to further thermally isolate the zones from the framework 201 and the shoulder screw 202. Similarly, the first insulative fiber washer 206 can provide a larger physical diameter to hold the spring 205 in place, to distribute force from compression, as well as to insulate the shoulder screw 202 from the spring 205, as the spring 205 is in direct contact with the thermal module base plate 203. When a microfluidic device is clamped to the overall thermal system, the microfluidic chip is secured to the device framework 201 such that the thermal module base plate 203 is pushed down, compressing the springs 205 in all of the thermal zones. The springs 205 thereby apply upward pressure to the zones of the microfluidic device. In alternative embodiments, the shape of the bearings 204 can be configured to have a flange in contact with the framework 201 that is sufficiently large enough to forgo the need for the second insulative fiber washer 206'.

The spring 205 addresses imperfect contact that may otherwise result due to variation in the construction of a microfluidic chip. The spring 205 applies a force to the bearing 204 that thereby places the thermal module, shown here in a simplified form as a single part thermal module base plate 203 (e.g. a heating element) in thermal contact with a microfluidic chip. Each thermal module can have a plurality of mechanisms for each zone, such that the spring force can be applied evenly across any load in a given zone. In some implementations, the thermal module can be configured to have two, three, four, five, six, or more mechanisms to apply a spring force as disclosed herein. In some aspects, the compression displacement of any spring 205 can be 0.1 mm, 0.2 mm, 0.5 mm, 1.0 mm, 1.5 mm, 2.0 mm, or any increment or gradient of length within that range. In further aspects, the compression displacement of any spring 205 can be less than 0.1 mm or greater than 2.0 mm.

In alternative embodiments of the thermal zone actuation mechanism, structures other than the coil springs 205 illustrated can be used, independently or in combination, to provide a force to ensure contact between a thermal zone sub-assembly and the microfluidic device. In some aspects, such alternatives can include: extension springs triggered by a binary or "flip" mechanism; elastomeric parts, such as parts made of rubber; flexure mechanisms; motors; pneumatic actuators; gas springs; Belleville springs; wave-type springs; disc-type springs; torsion springs; counterweights; magnets; memory alloy; or in embodiments where a thermal source and a heat spreader is positioned above the microfluidic device, gravity.

In many embodiments of the thermal zone actuation mechanism, the bearing 204 can be a polymer bearing. The bearing 204 can alternatively be constructed as: a metal bushing, optionally lubricated with an oil or polymer coated; a flexure mechanism; or a ball bearing sleeve. In further alternative embodiments, the shoulder screw 202, or a bracket coupled to the shoulder screw 202, can be a plastic component impregnated with plastic or oil, where the bracket has a plain hole that functions as a bushing, and the configuration does not include a separate bearing.

Figure 2B:
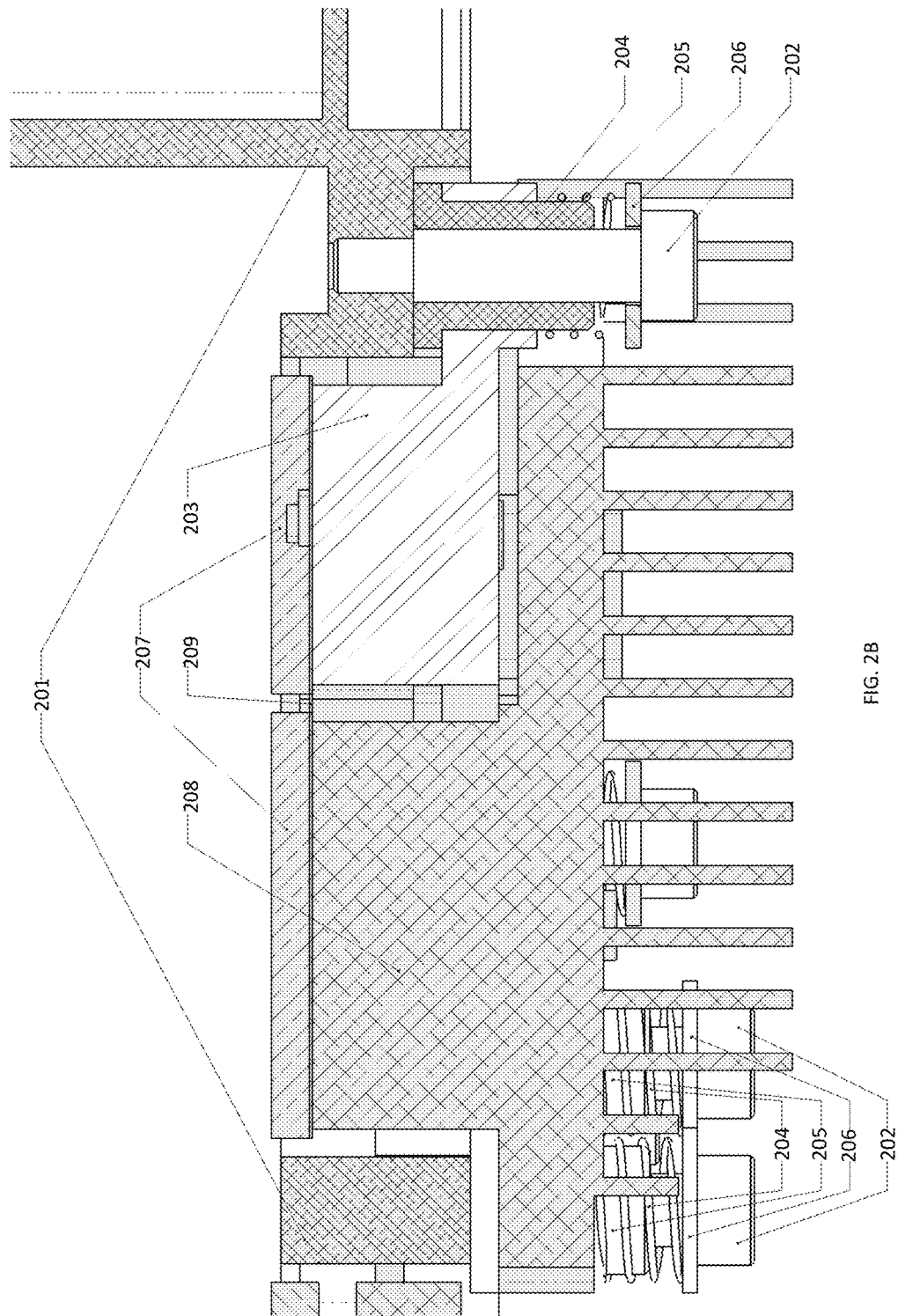
FIG. 2B is a cross-sectional schematic view of a region of a thermal management device used for microfluidic chip PCR, having a plurality of thermal zone actuation mechanisms, according to aspects of the present disclosure.

FIG. 2B is a cross-sectional schematic view of two thermal control zones of a thermal management device used for microfluidic chip PCR, having a plurality of heat zone actuation mechanisms located across the thermal control zones. As illustrated in FIG. 2B, the bearing 204 surrounding the shoulder screw 202 has a flange in contact with the framework 201 that provides for contact and the distribution of force that may be applied from the framework 201 or from the spring 205 coupled to the bearing 204. Further illustrated are thermal spreaders 207 (alternatively referred to as heat spreaders) over which a microfluidic plate can reside during a PCR operation. Below one thermal spreader 207 (right side) is the insulative thermal module base plate 203, providing for temperature control by inhibiting the transmission of heat away from that thermal spreader. Below the other thermal spreader 207 (left side) is a heat sink thermal module base plate 208. Each thermal spreader 207 is thermally coupled to a heater element 209, where the heater element 209 can be a flexible, resistive heater element, and can further have two, three, or more heating zones that can be set to different temperatures or to the same temperature. In further implementations the heater element 209 could instead be multiple elements.

The heater element 209 can be a single, flexible, body which contains multiple, independently controlled heating zones. Accordingly, the heater element 209 can raise the temperature of the one or more thermal spreaders 207 to specific temperatures or temperature ranges, the various thermal zone actuation mechanisms can provide an upward force to ensure that each thermal spreader 207 is in direct contact with corresponding regions on a microfluidic chip, where the contact is generally uniform and with an equal force across the area of the thermal spreader 207. Further, the framework 201 can provide for positional control between different thermal spreaders 207 or other thermal control zone sub-assemblies. The thermal spreaders 207 can further include channels to allow for wires connected to thermistors coupled to the sub-assembly, where the thermistors can be on either or both of the top and the bottom side of the thermal spreaders 207. In some implementations, the thermal spreaders 207 can be made of copper, other conductive metals or alloys, or polymeric gap pad materials. In further implementations, the thermal spreader 207 can be sufficiently flexible such that individual thermal spreaders 207 are not needed for each thermal zone, but rather a single thermal spreader 207 can extend across two or more thermal zones and flex accordingly when actuated into a position in contact with a microfluidic device.

In further alternative embodiments of the thermal zone actuation mechanisms used for thermal management device, the orientation of the shoulder screw 202 and the bearing 204 can be swapped. In such a configuration, the shoulder screw 202 can be referred to as a shaft, and the bearing 204 can be referred to as a bushing, where the bushings are mechanically coupled to the framework 201, and the shaft can be mechanically coupled to other support structures, such as brackets.

Thermal control zones in the device that are required to reach high temperatures often use resistive heating, thermoelectric elements (Peltier), infrared, heated fluids, or other heating methods. For example, a thermal control zone (such as the denaturing zone) that is raised to 95° C. can use a resistive heating element mounted on a bracket made of a rigid insulating material such as Garolite-reinforced phenolic in order to reduce undesired heat transfer to the environment. In some embodiments, one or two other thermal control zones that are raised to a temperature of about 65° C. (such as the primary hybridization zone) and about 55° C. (such as the secondary hybridization zone), but situated proximate to a thermal control zone set at 95° C. (with small gaps, for example 1 mm between the zones), can be mounted on finned heat sinks to increase their thermal mass and rate of heat transfer to the environment. These finned heat sinks coupled to the thermal control zones set at 65° C. and 55° C. can help dissipate heat transferred from a neighboring 95° C. zone, and also allow for easier control of the temperature of the zones, as the heat sinks increase the rate of cooling. In other words, having heat sinks on relatively high temperature zones allows them to cool faster in case the user or process controller requests a lower temperature, and also makes it more difficult for the heater controller to overshoot the desired temperature.

Thermal zones with intermediate temperatures may be required to have different functions. For example, a thermal control zone set at about 35° C. can be used to heat its own thermal control zone using a resistive or thermoelectric element. Alternatively, a thermal control zone set at about 35° C. can be used to act as heat sink to remove/transfer heat neighboring relatively warmer thermal control zones. Another example is where two thermal control zone are configured to be proximate to reagent reservoirs, where the reagents need be preserved at or below room temperature (e.g. at 22° C.). Such thermal control zones are cooled by individual thermoelectric elements or other cooling methods.

Alternative heating or cooling elements that can be used for the disclosed thermal control zones include, but are not limited to: silicone resistive heaters; ceramic resistive heaters; Stirling engines; liquid nitrogen, dry ice, or other phase change materials; liquid cooling or liquid heating circuits; and infrared lighting such as "heat lamps". Further applications for cooling thermal zones include: a fan or other air source blowing directly on the surface of a thermal control element; liquid cooling; use of the chassis connected to the thermal control element as a cooling heat sink; and/or tubing with cooling gas in contact with the a heated zone to provide for a thermal exchange conduit (e.g. as in refrigerators).

Figure 3:
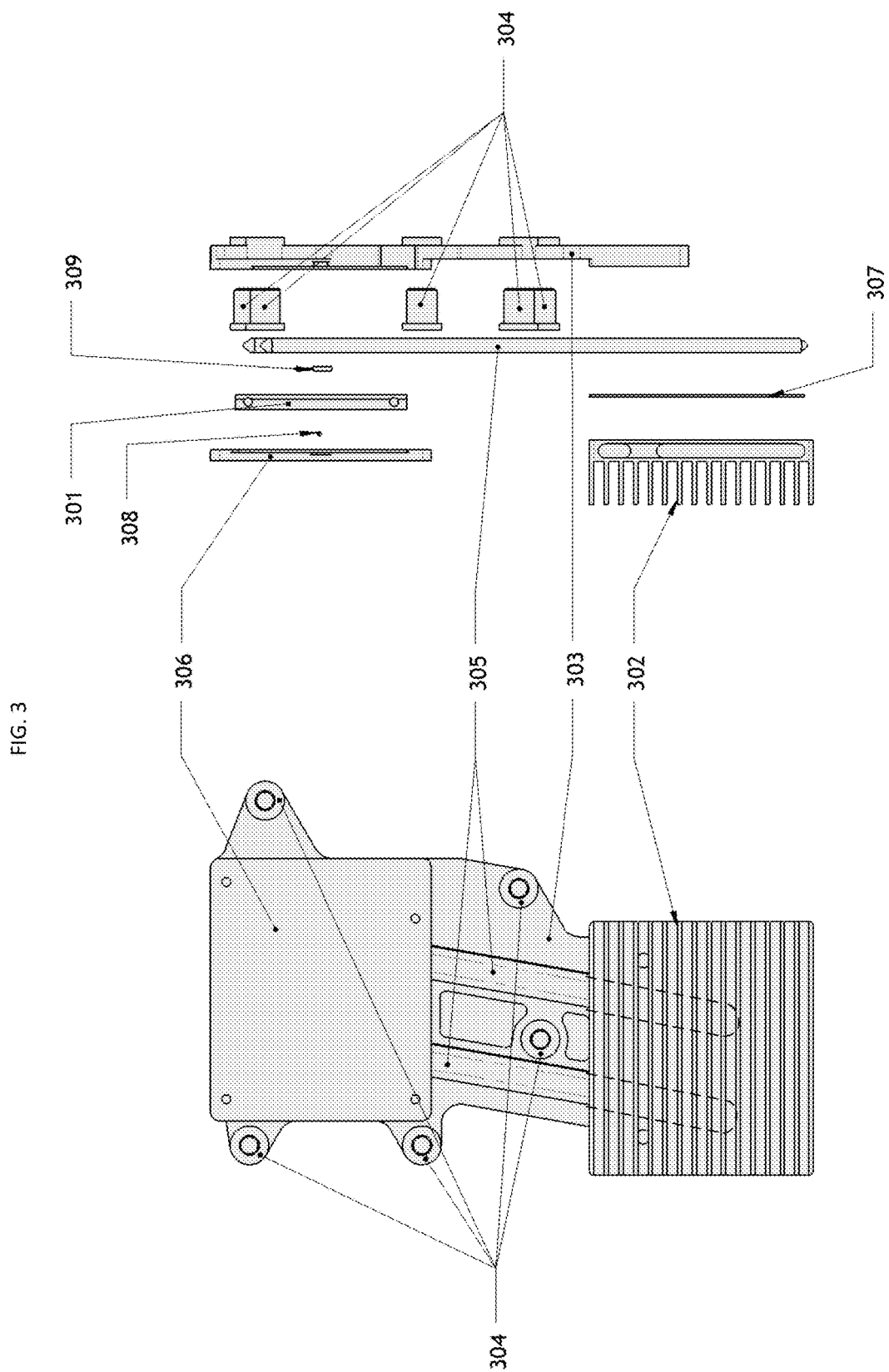
FIG. 3 is a schematic design illustration of an exemplary thermal zone sub-assembly with a remotely-mounted heat sink, with an exploded schematic illustration of the same, according to aspects of the present disclosure.

FIG. 3 is a schematic design illustration of an exemplary thermal zone sub-assembly 300 with a remotely-mounted heat sink 302. In some embodiments, the thermal zone sub-assembly 300 can be one of the thermal control zone sub-assemblies that maintains a lower temperature relative to one or more of neighboring thermal control zone sub-assemblies. When in contact with a microfluidic device, a thermoelectric module 301 (as part of the thermal zone sub-assembly 300) can conduct heat into a region of the microfluidic device. The thermal zone sub-assembly 300 transfers excess or waste heat from the thermoelectric module 301 to a remote heat sink 302. In various aspects, this configuration and structure can be utilized where there is otherwise insufficient space to directly attach a heat sink to the thermoelectric module 301. The thermoelectric module 301 and the remote heat sink 302 can also attach to a bracket 303 (shown as thermal module body 203 in FIG. 2A). Through this bracket 303, a number of heat pipes 305 can be used to conduct the waste heat away from the thermoelectric module 301 through a relatively small space, and at a higher rate than can be achieved by conduction alone through a solid material. The heat sink 302 can be attached to the end of these heat pipes 305 opposite from the thermoelectric module 301, in an area where there is enough clearance for a heat sink 302 of sufficient size and thermal capacity.

In some aspects, the thermal zone sub-assembly 300 can also include a heat spreader 306, arranged such that the microfluidic device is not in direct contact with the thermoelectric module 301, but rather arranged such that thermoelectric module 301 (or other heat control element) can be spread across a larger area than occupied by the thermoelectric module 301 alone. In other words, the heat from the thermal control element of the thermal zone sub-assembly 300 is conducted to a surface, that, in this case, has a larger surface area than that of the element itself and can heat a corresponding area of a microfluidic device. The polymer bushings 304 that are part of the actuation mechanism are also shown in this diagram.

A thermal interface material 307 can be in contact with both the heat sink 302 and the heat pipes 305 and positioned to ensure thermal conduction between the heat sink 302 and the heat pipes 305. Further, a top side thermistor 308 and a bottom side thermistor 309 can be positioned above and below, respectively, the thermoelectric module 301 to monitor the temperature of that thermoelectric module 301 and that respective thermal sub-assembly. One or more of such thermistors can be in communication with a control system or controller to adjust the temperature, or stop the operation, of the thermoelectric module 301. In some applications, a thermal grease can be used on the thermoelectric module 301 to ensure conduction on one side or both sides of the thermoelectric module 301.

Figure 4:
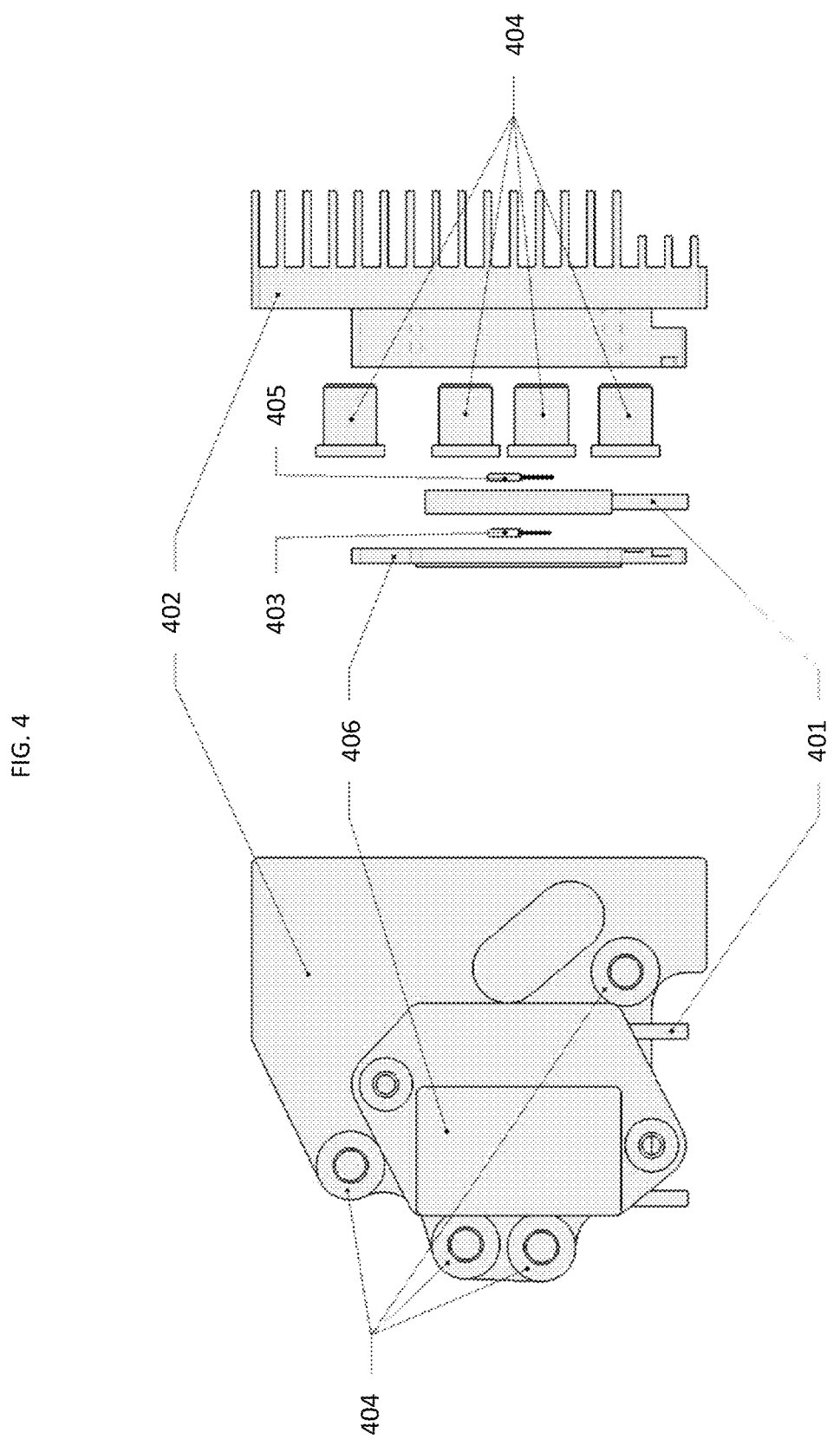
FIG. 4 is a schematic design illustration of an exemplary thermal zone sub-assembly with a directly-mounted heat sink, with an exploded schematic illustration of the same, according to aspects of the present disclosure.

FIG. 4 is a schematic design illustration of an exemplary thermal zone sub-assembly with a directly-mounted heat sink. In some embodiments, the thermal zone sub-assembly 400 can be one of the thermal control zone sub-assemblies that maintains a lower temperature relative to one or more of neighboring thermal control zone sub-assemblies. When in contact with a microfluidic device, a thermoelectric module 401 (as part of the thermal zone sub-assembly 400) can conduct heat into a region of the microfluidic device. The thermal zone sub-assembly 400 transfers excess or waste heat from the thermoelectric module 401 to a directly-mounted heat sink 402. In various aspects, this configuration and structure can be utilized where there is sufficient space to directly attach a heat sink 402 to the thermoelectric module 401.

In some aspects, the thermal zone sub-assembly 400 can also include a heat spreader 406, arranged such that the microfluidic device is not in direct contact with the thermoelectric module 401, but rather arranged such that thermoelectric module 401 (or other heat control element) can be spread across a smaller area than occupied by the thermoelectric module 401 alone. In other words, the heat transfer from the thermal control element of the thermal zone sub-assembly 400 is conducted to a surface, that, in this case, has a smaller surface area than that of the element itself and can transfer heat to a corresponding area of a microfluidic device. The polymer bushings 404 that are part of the actuation mechanism are also shown in this diagram.

Further, a top side thermistor 403 and a bottom side thermistor 405 can be positioned above and below, respectively, the thermoelectric module 401 to monitor the temperature of that thermoelectric module 401 and that respective thermal sub-assembly. One or more of such thermistors can be in communication with a control system or controller to adjust or stop the operation of the thermoelectric module 401. In some applications, a thermal grease can be used on the thermoelectric module 401 to ensure conduction on one side or both sides of the thermoelectric module 401.

Figure 5:
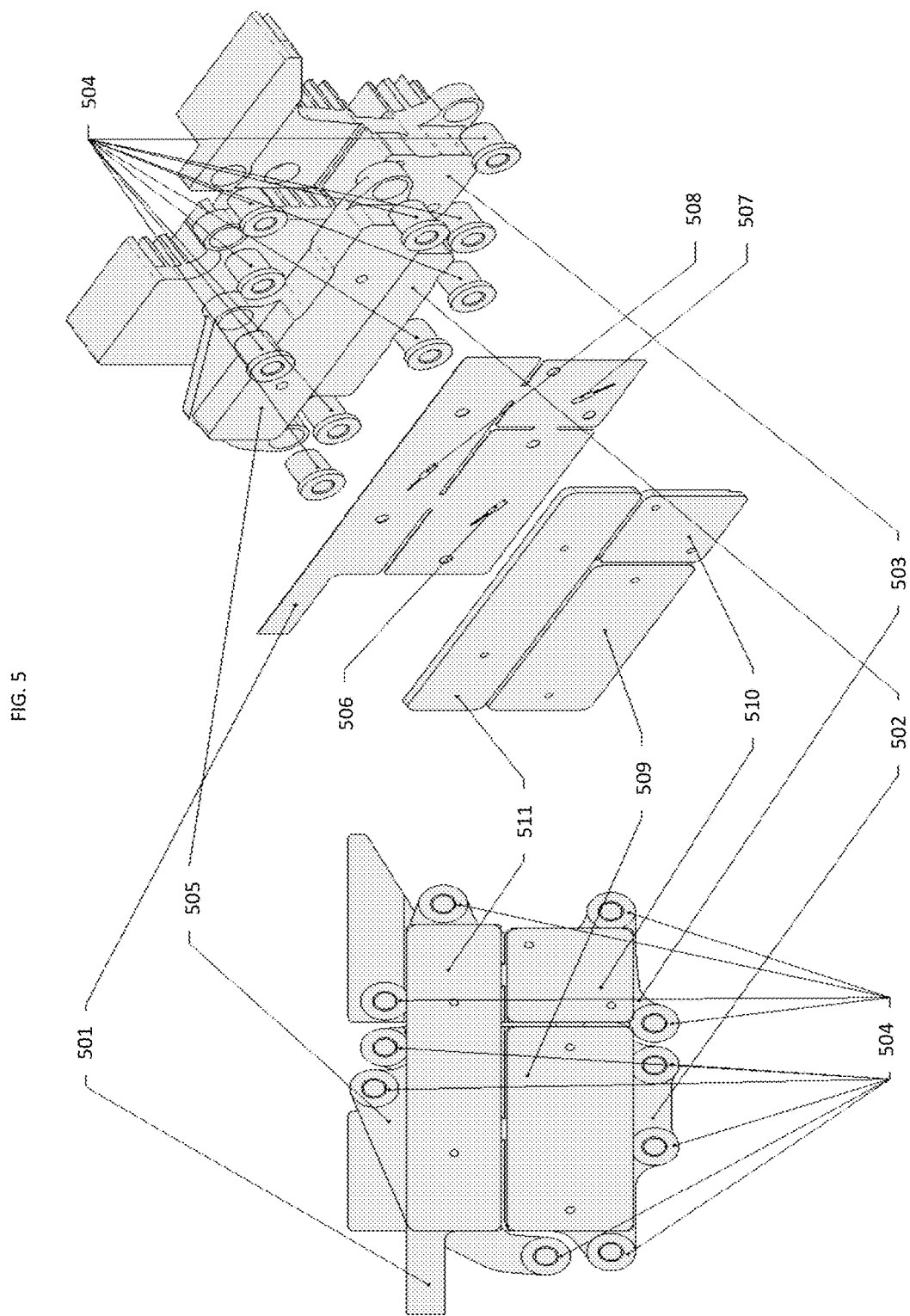
FIG. 5 is a schematic design illustration of an exemplary resistive multiple thermal zone assembly, with an exploded schematic illustration of the same, according to aspects of the present disclosure.

FIG. 5 is a schematic design illustration of an exemplary resistive multiple thermal zone assembly. A flexible heater circuit 501 (shown as heater element 209 in FIG. 2B), is positioned between a set of heat spreading elements and a corresponding set of thermal actuation mechanisms in respective thermal zone sub-assemblies. As illustrated, the flexible heater circuit 501 has three connected but structurally distinct regions, which can each be set to the same or different temperatures. In other embodiments, the flexible heater circuit 501 can be configured to have two connected but structurally distinct regions, and in other embodiments the flexible heater circuit 501 can be configured to have four or more connected but structurally distinct regions. In alternative embodiments, the flexible heater circuit 501 can be configured to have a single region. Positioned below the flexible heater circuit 501 is a first heat sink 502, and a second heat sink 503 (shown as heat sink thermal module base plate 208 in FIG. 2B), and an insulative thermal module body 505 (shown as insulative thermal module body 203 in FIG. 2A and 2B), where the first heat sink 502 can be directly mounted to the flexible heater circuit 501 and the second heat sink 503 can be remotely coupled to the flexible heater circuit 501, such that the individual heat sinks and insulative thermal module bodies correspond to the different heat zones. Polymer bearings 504 indicate the locations of thermal zone actuation mechanisms that can apply force to move the individual thermal zone modules to place the first heat spreader element 509, second heat spreader element 510, and third heat spreader element 511 in contact with a microfluidic device. Each region of the flexible heater circuit 501 is connected by relatively small tabs of material, allowing each zone to move independently when driven by respective thermal zone actuation mechanisms. In some aspects, each zone of the flexible heater circuit 501 can move or flex a distance of up to about 0.75 mm to 1.0 mm with respect to the other zones of the flexible heater circuit 501.

Located in between the first heat spreader element 509, second heat spreader element 510, and third heat spreader element 511 and the flexible heater circuit 501 are a first thermistor 506, a second thermistor 507, and a third thermistor 508, each located within a different zone of the flexible heater circuit 501. These thermistors can monitor the temperature of the flexible heater circuit 501 and respective thermal sub-assemblies connected to the flexible heater circuit 501. One or more of such thermistors can be in communication with a control system or controller to adjust temperature, or stop the operation, of one or more of the zones of the flexible heater circuit 501. Positioned above the flexible heater circuit 501 is first heat spreader 509, a second heat spreader 510, and a third heat spreader 511. When the corresponding thermal zone actuation mechanisms are engaged, a corresponding region or regions of the flexible heater circuit 501 can be moved (via the polymer bearings 504) into direct contact with one or more of the first heat spreader 509, second heat spreader 510, and third heat spreader 511. Each thermal zone assembly moves in unison when actuated, as the components are rigidly mounted together, albeit with the flexible heater circuit 501 spread across as a component of more than one thermal zone assembly. (For example, as shown in FIG. 5, there are three individual thermal zone assemblies identified by the arrangement of elements: 509-506-501-505, 510-507-501-503, and 511-508-501-505). A microfluidic device in contact with one or more of the first heat spreader 509, second heat spreader 510, and third heat spreader 511 can thereby be heated (or in some aspects, cooled) to a temperature as determined by the corresponding region of the flexible heater circuit 501.

In some exemplary aspects, the flexible heater circuit 501 can be controlled to have each region set to a different temperature, where the thermal zones can be characterized as being "low temperature", "medium temperature", and "high temperature" relative to each other. For example, the flexible heater circuit 501 can be configured such that the first heat spreader 509 acts as a low temperature heat spreader, the second heat spreader 510 acts as a medium temperature heat spreader, and the third heat spreader 511 acts as a high temperature heat spreader. Regions of a microfluidic device resting on or otherwise coupled to the heat spreader elements can thus rise (or in some aspects, drop) in temperature to reach the temperature of the proximate region of the flexible heater circuit 501.

In further embodiments, the entire thermal management device, or portions thereof, can be covered by a thin, thermally conductive membrane in order to help seal any or all of the physical gaps in the assembly. Such a seal can prevent liquids from leaking into or out of the assembly.

As noted above, many of the heating elements are directly mounted to finned heat sinks to increase thermal mass and facilitate convective heat transfer from the zones to the environment. In some configurations, such zones are constrained in physical space by separate assembly, and have no physical room to be directly mounted heat sinks. These zones use heat pipes to transfer heat to remote heat sinks, an example of which is illustrated in FIG. 3.

As also noted above, physically isolating and insulating each thermal zone in the thermal management device, by creating separate modules for each zone, ensures that the most efficient path of thermal conduction between each zone is the attached microfluidic device itself. The microfluidic device can be made out of a polymer that is a poor thermal conductor, and therefore ensures that there is only a small amount thermal transfer between the zones. This way, the temperature of each zone can stay fairly uniform and constrained to the specified thermal zones.

Figure 6:
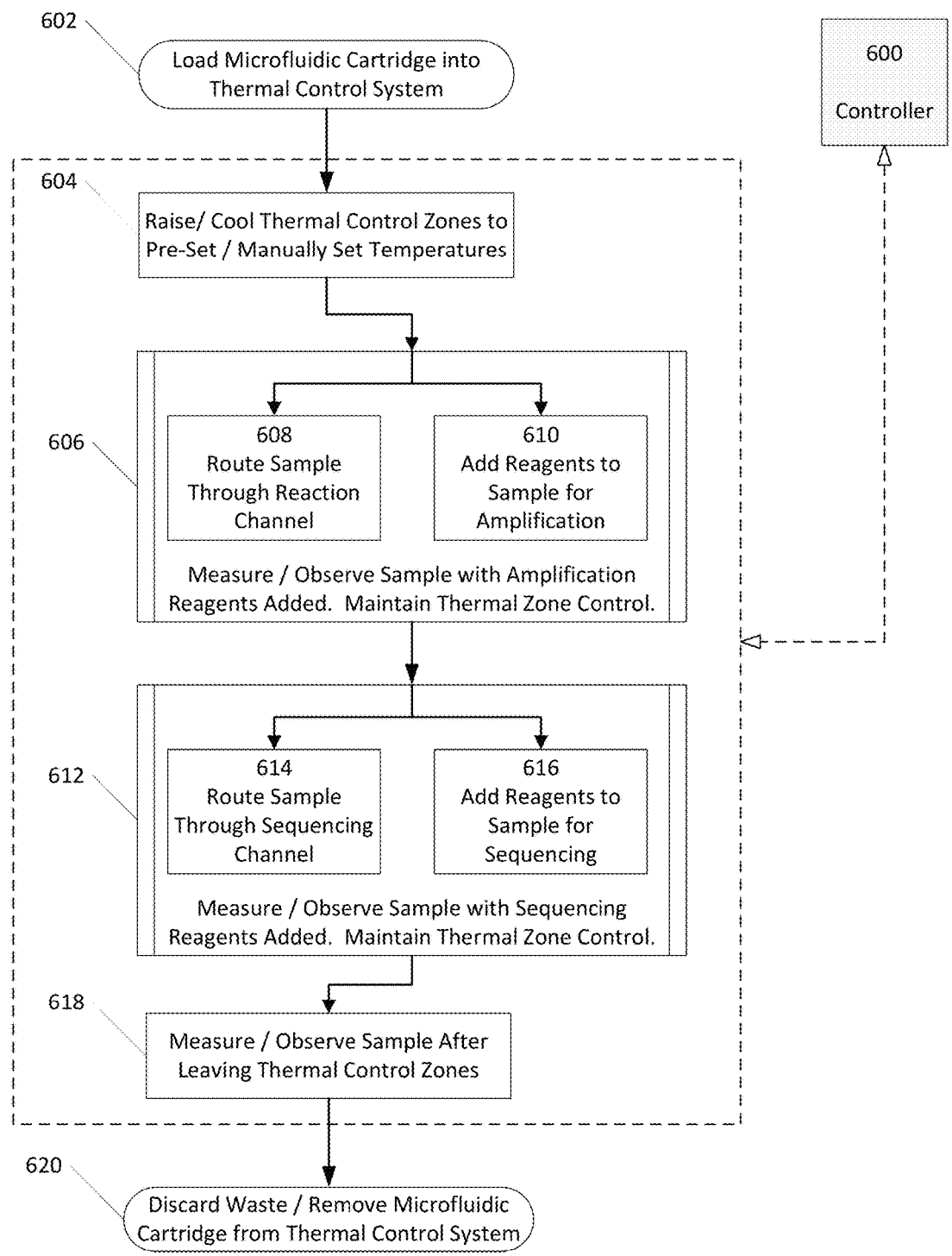
FIG. 6 is a flowchart of an exemplary process for thermal control of PCR using a thermal management device, according to aspects of the present disclosure.

FIG. 6 is a flowchart of an exemplary process for thermal control of and thermal management device used for PCR. Generally, a controller 600 is operationally coupled to the thermal management device, where the controller 600 is configured to relay instructions to, and receive sensory data (such as temperature) from, the thermal management device and components thereof. In some aspects, the controller 600 can include a user interface to allow an operator to directly or manually control operation of the thermal management device. The controller 600 can be a non-transitory, computer-readable media, further configured to store and execute programmed operational instructions to components of the thermal management device. In some embodiments, the controller 600 can be electronically coupled to: heating and/or cooling elements in individual thermal control zones, thermal zone actuation mechanisms, and sensors (such as thermistors or optical detectors) that are part of the thermal management device. In other embodiments, the controller 600 can further be operationally and electronically coupled to a microfluidic device such that the controller 600 can, in part, control the introduction and flow of reagents and/or sample into the channels of the microfluidic device, when the microfluidic device is coupled and proximate to the thermal management device.

In the exemplary process, at step 602, a microfluidic cartridge (alternatively referred to as a chip or a plate) is loaded into a thermal control system, and mechanically positioned or coupled to a proximate thermal management system. The microfluidic chip can hold sample in one or more reservoirs, or sample can be added to the microfluidic chip once loaded into the thermal control system. At step 604, individual thermal control zones of the thermal management system can be raised or lowered to manually set, or pre-set, temperatures. At step 606, the sample is moved from the reservoir into a reaction channel region of the microfluidic chip. At step 608, one or more reagents can be added to the sample at the same reaction region or reaction channel of the microfluidic chip, where such reagents can be PCR reagents for amplification of the sample. At step 610, the sample and any added reagents are routed through the reaction channel region in the microfluidic chip. The processes of step 608 and step 610 can run concurrently as additional sample and reagent are added to the microfluidic channel. Within step 606, the addition and reaction of the reagents (e.g. amplification reagents for PCR) with the sample can be observed and/or measured by a first sensor, such as an optical detector. Further, during step 606, the temperature of the sample and reagents are controlled as the sample fluid passes proximate to the thermal control zones of the thermal management system, which in some aspects can be controlled such that the sample and reagent fluids can undergo amplification reactions.

At step 612, the (amplified) sample is moved further from the reaction channel region of the microfluidic chip and toward a sequencing channel region of the microfluidic chip. At step 614, one or more reagents can be added to the sample at the same sequencing channel region of the microfluidic chip, where such reagents can be enzyme for sequencing of the sample. At step 616, the sample and any added reagents are routed through the sequencing channel region in the microfluidic chip. The processes of step 614 and step 616 can run concurrently as additional sample and reagent are added to the microfluidic channel. Within step 612, the addition and reaction of reagents (e.g. sequencing reagents such as enzyme) with the sample can be observed and/or measured by a second sensor, such as an optical detector. Further, during step 612, the temperature of the sample and reagents are controlled as the sample fluid passes proximate to the thermal control zones of the thermal management system, which in some aspects can be controlled such that the sample and reagent fluids can undergo sequencing reactions At step 618, after the sample fluid has left the thermal control zones (or in other words, once the amplified and sequenced sample fluid has entered a region of the microfluidic channel(s) not proximate to the thermal control zones), the sample can be observed and/or measured by a sensor, such as an optical detector, alternatively referred to as a final sensor or sequencing sensor. At step 620, following observation/measurement, the sample can be routed to a discard reservoir and the microfluidic cartridge can be removed from the thermal control system.

In alternative embodiments of the present disclosure, a thermal management device enabling PCR reactions in a microfluidic channel can include a framework having a channel and one or more isolated, movable and conductive thermal zone sub-assemblies that are attached to the framework via thermal insulative bearings and fasteners, where each thermal zone sub-assembly can be heated or cooled to a temperature suitable for PCR reactions. In some aspects, the fasteners can be shoulder screws. In other aspects, the thermal insulative bearings can be polymer-based bearings. In further aspects, each of the thermal zone sub-assemblies can contain at least one polymer-based bearing, which travels up and down on the shaft of at least one of the shoulder screws that attached to the framework, and can be pushed upward by one or more springs. In some such aspects, each of the thermal zone sub-assemblies can contain one polymer-based bearing that can be attached to the framework via one shoulder screw and can be pushed upward by one spring. In further embodiments, each of the thermal zone assembly can further include a first insulative fiber washer around the shoulder screw and in between the thermal zone sub-assembly and the framework, with a second insulative fiber washer that holds the spring in place, where when a microfluidic device is clamped to the thermal management device, each of the thermal zone sub-assemblies can be pushed down compressing the spring, thereby applying upward pressure to contact the microfluidic device. In some aspects, each individual thermal zone sub-assembly can have a minimal spacing of one millimeter (1 mm) between itself and any other thermal zone sub-assembly, or the framework. In other aspects, at least one thermal zone assembly can have a resistive heating element. In some further aspects, where the at least one thermal zone assembly has a resistive heating element, the heating element can be used to maintain a thermal zone at a temperature above room temperature. In other aspects, at least one thermal zone assembly can have a thermoelectric element. In further aspects, at least one thermal zone sub-assembly that has a thermoelectric element can be used to maintain a thermal zone at a temperature at or below room temperature. In some aspects, at least one of the thermal zone sub-assembly can be mounted on a heat sink, where in various aspects the heat sink can be a finned heat sink. In yet further aspects, at least one of the thermal zone subassembly can be connected to a remote heat sink via at least one heat pipe. In other aspects, at least one of the thermal zone sub-assemblies can have a thermal electric element and includes a heat spreader surrounding the thermal electric element to spread the heat from the element to the surface of the heat spreader.

In alternative embodiments of the present disclosure, a method to perform PCR reactions in a microfluidic device is disclosed, including the steps of providing a thermal management device as described herein, the device containing a plurality of droplets that contain reagents necessary for desired PCR reactions, and performing PCR in the device.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A thermal management device enabling PCR reactions in a microfluidic channel, the device comprising:
   a framework;
   one or more thermal zone sub-assemblies coupled to the framework, each thermal zone sub-assembly having a thermal control element, and wherein each thermal zone sub-assembly is coupled to the framework by one or more thermal actuation mechanisms; and
   one or more thermal spreaders configured to contact the thermal control elements of the one or more thermal zone sub-assemblies,
   wherein the thermal actuation mechanisms consist essentially of insulative bearings, fasteners, and a spring, wherein the spring is configured to apply a force to drive the thermal control element toward one of the one or more thermal spreaders, wherein each fastener is a shoulder screw, and wherein each thermal actuation mechanism includes at least one polymer-based bearing, which travels up and down on the shaft of at least one of the shoulder screws that are attached to the framework and are pushed by the spring.

2. The thermal management device of claim 1, wherein the insulative bearings are polymer-based bearings.

3. The thermal management device of claim 1, wherein each thermal control element can be configured to have an operational temperature of from about 22° C. to about 95° C.

4. The thermal management device of claim 1, wherein each of the thermal actuation mechanisms further comprises a first insulative fiber washer around a shoulder screw that holds the spring in place.

5. The thermal management device of claim 1, wherein each thermal zone sub-assembly has a minimal spacing of 1 mm between itself and any other thermal zone sub-assembly or the framework.

6. The thermal management device of claim 1, wherein at least one thermal zone assembly has a resistive heating element used to maintain a thermal zone at a temperature above room temperature.

7. The thermal management device of claim 1, wherein at least one thermal zone assembly that has a thermoelectric element used to maintain a thermal zone at a temperature at or below room temperature.

8. The thermal management device of claim 1, wherein at least one thermal zone assembly maintains a thermal zone at a temperature above room temperature, and wherein at least another thermal zone assembly maintains a thermal zone at a temperature at or below room temperature.

9. The thermal management device of claim 8, wherein a first thermal zone and a fifth thermal zone are maintained at a temperature at or below room temperature, wherein a second thermal zone, fourth thermal zone, and a sixth thermal zone are maintained at a temperature above room temperature, and wherein a third thermal zone is maintained at a temperature above the temperature of at least the second thermal zone.

10. The thermal management device of claim 1, wherein at least one of the thermal zone sub-assemblies is coupled to a heat sink.

11. The thermal management device of claim 10, wherein the heat sink is a finned heat sink.

12. The thermal management device of claim 10, wherein at least one of the thermal zone sub-assemblies is remotely connected to the heat sink via a heat pipe.

13. The thermal management device of claim 10, wherein at least one of the thermal zone sub-assemblies is directly mounted on the heat sink.

14. The thermal management device of claim 1, wherein a flexible heater circuit is configured and arranged to be the thermal control element for two or more thermal zone sub-assemblies of the thermal management device.

15. The thermal management device of claim 14, wherein a first region of the flexible heater circuit can be moved by one of the thermal actuation mechanisms to be in contact with one of the thermal spreaders.

16. The thermal management device of claim 15, wherein the first region of the flexible heater circuit is contact with one of the thermal spreaders and at least a second region of the flexible heater circuit is in contact with another one of the thermal spreaders.

17. The thermal management device of claim 16, wherein the first region of the flexible heater circuit and the second region of the flexible heater circuit can flex relative to each other by a distance of about 0.75 mm to about 1.0 mm.

18. A method to perform PCR reactions in a microfluidic device comprising the following steps:
(a) providing a thermal management device comprising:
a framework;
one or more thermal zone sub-assemblies coupled to the framework, each thermal zone sub-assembly having a thermal control element, and wherein each thermal zone sub-assembly is coupled to the framework by one or more thermal actuation mechanisms; and
one or more thermal spreaders configured to contact the thermal control elements of the one or more thermal zone sub-assemblies, wherein the thermal actuation mechanisms consist essentially of insulative bearings, fasteners, and a spring, wherein the spring is configured to apply a force to drive the thermal control element toward one of the one or more thermal spreaders, wherein each fastener is a shoulder screw, and wherein each thermal actuation mechanism includes at least one polymer-based bearing, which travels up and down on the shaft of at least one of the shoulder screws that are attached to the framework and are pushed by the spring, and further wherein the thermal management device contains a plurality of droplets that contain reagents necessary for desired PCR reactions, and
(b) performing PCR in the microfluidic device.

19. A thermal management device enabling PCR reactions in a microfluidic channel, the device comprising:
a framework;
one or more thermal zone sub-assemblies coupled to the framework, each thermal zone sub-assembly having a thermal control element, and wherein each thermal zone sub-assembly is coupled to the framework by one or more thermal actuation mechanisms;
one or more thermal spreaders configured to contact the thermal control elements of the one or more thermal zone sub-assemblies; and
a flexible heater circuit, configured and arranged to be the thermal control element for two or more thermal zone sub-assemblies of the thermal management device,
wherein a first region of the flexible heater circuit can be moved by one of the thermal actuation mechanisms to be in contact with one of the thermal spreaders, wherein at least a second region of the flexible heater circuit is in contact with another one of the thermal spreaders, and wherein the first region of the flexible heater circuit and the second region of the flexible heater circuit can flex relative to each other by a distance of about 0.75 mm to about 1.0 mm.

20. The thermal management device of claim 19, further wherein the thermal actuation mechanisms consist essentially of insulative bearings, fasteners, and a spring, wherein the spring is configured to apply a force to drive the thermal control element toward one of the one or more thermal spreaders, wherein each fastener is a shoulder screw, and wherein each thermal actuation mechanism includes at least one polymer-based bearing, which travels up and down on the shaft of at least one of the shoulder screws that are attached to the framework and are pushed by the spring.

* * * * *